US012747465B2

(12) United States Patent
Maruyama et al.

(10) Patent No.: US 12,747,465 B2
(45) Date of Patent: Sep. 29, 2026

(54) METHOD FOR ANALYZING PROTEIN

(71) Applicant: HITACHI, LTD., Tokyo (JP)

(72) Inventors: Masashi Maruyama, Tokyo (JP); Eric Ofosu-Twum, Tokyo (JP); Akihiro Nojima, Tokyo (JP); Masuyuki Sugiyama, Tokyo (JP); Shun Kumano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 601 days.

(21) Appl. No.: 18/299,955

(22) Filed: Apr. 13, 2023

(65) Prior Publication Data

US 2023/0416301 A1 Dec. 28, 2023

(30) Foreign Application Priority Data

May 12, 2022 (JP) ................................ 2022-078934

(51) Int. Cl.

| | |
|---|---|
| ***C12Q 1/37*** | (2006.01) |
| ***C07K 1/12*** | (2006.01) |
| ***C12N 9/76*** | (2006.01) |
| ***G01N 30/72*** | (2006.01) |
| ***G01N 30/88*** | (2006.01) |
| ***G01N 33/68*** | (2006.01) |

(52) U.S. Cl.

CPC .................. *C12Q 1/37* (2013.01); *C07K 1/12* (2013.01); *G01N 30/72* (2013.01); *G01N 33/6803* (2013.01); *C12N 9/6427* (2013.01); *C12Y 304/21004* (2013.01); *C12Y 304/24027* (2013.01); *G01N 2030/8831* (2013.01); *G01N 33/6848* (2013.01)

(58) Field of Classification Search

CPC ...... C07K 1/12; G01N 30/72; G01N 33/6803; G01N 33/6848; G01N 2030/8831; C12N 9/6427; C12Y 304/21004; C12Y 304/24027

See application file for complete search history.

(56) References Cited

U.S. PATENT DOCUMENTS 7,288,382 B2 * 10/2007 Harbury ............. G01N 33/6818 435/7.1
11,129,790 B2 * 9/2021 Zhou .................... C12N 9/1044
2018/0369131 A1 12/2018 Zhou et al.

FOREIGN PATENT DOCUMENTS

WO WO 2015/179714 A1 11/2015

OTHER PUBLICATIONS

"Development and Application of Mass Spectrometry-Based Protein Footprinting in Structural Proteomics", a dissertation by Ming Cheng, Washington University in St. Louis, earliest available date of Jun. 5, 2020, accessed via Wayback Machine. doi.org/10.7936/aztc-zt80 (Year: 2020).*

Bark et al. 2001. "High-temperature protein mass mapping using a thermophilic protease". Journal of the American Chemical Society, 123(8):1774-1775. DOI: 10.1021/ja002909n (Year: 2001).*

Yen et al. 2017. Ligand binding to a G protein-coupled receptor captured in a mass spectrometer. Science Advances. 3(6):e1701016. DOI: 10.1126/sciadv.1701016. (Year: 2017).*

Limpikirati et al. 2019. "Covalent Labeling with Diethylpyrocarbonate: Sensitive to the Residue Microenvironment, Providing Improved Analysis of Protein Higher Order Structure by Mass Spectrometry". Anal Chem. 91(13):8516-8523 DOI: 10.1021/acs.analchem.9b01732. (Year: 2019).*

Xu, G., Hydroxyl Radical-Mediated Modification of Proteins as Probes for Structural Proteomics, Chemical Reviews, vol. 107, No. 8, pp. 3514-3543 (2007).

Jones, A. X., et al., "Improving mass spectrometry analysis of protein structures with arginine-selective chemical cross-linkers," Nature Communications, vol. 10, No. 1, pp. 1-11 (2019).

Bark, S. J., et al., "High-Temperature Protein Mass Mapping Using a Thermophilic Protease," J. Am. Chem. Soc., vol. 123, No. 8, pp. 1774-1775 (2001).

Mendoza, V.L., et al., "Probing Protein Structure by Amino Acid-Specific Covalent Labeling and Mass Spectrometry," Mass Spectrometry Reviews, vol. 28, No. 8, pp. 785-815 (2009).

Extended European Search Report, mailed Oct. 9, 2023, for European Application No. 23167503.4.

Notice of Reasons for Refusal, mailed Feb. 3, 2026, for Japanese Application No. 2022-078934 (with English translation).

* cited by examiner

*Primary Examiner* — Anand U Desai
*Assistant Examiner* — Andrew T Moehlman
(74) *Attorney, Agent, or Firm* — Baker Botts L.L.P.

(57) ABSTRACT

Provided is a pretreatment method for structural analysis of a protein, including chemical modifying and fragmenting a protein to be analyzed, in which in the fragmenting, the protein is treated at a temperature of 60 to 99° C. in the presence of a heat-resistant protease that has four or more cleavage sites and is soluble or immobilized on a carrier.

5 Claims, 2 Drawing Sheets

Specification includes a Sequence Listing.

METHOD FOR ANALYZING PROTEIN

SEQUENCE LISTING

The instant application contains a Sequence Listing which has been submitted electronically in XML format and is hereby incorporated by reference in its entirety. Said XML copy, created on Jun. 23, 2023, is named 072388_1602_SL_2.xml and is 1,858 bytes in size.

BACKGROUND OF THE INVENTION

1. Field of the Invention

The present invention relates to a pretreatment method in protein analysis and a method for analyzing a protein using the method.

2. Description of the Related Art

Macrobiomolecules, such as proteins, have complex higher order structure, thereby exhibiting interactions with other biomolecules. Understanding of such interactions between biomolecules and complex formation is important for elucidating a mechanism of a complicated phenomenon in a living body, pharmaceutical development, and the like.

Techniques such as single crystal structure analysis, nuclear magnetic resonance spectroscopy (NMR), surface plasmon resonance (SPR), quartz crystal microbalance (QCM), and imaging mass cytometry (IMC) have been developed as techniques for analyzing interactions between biomolecules, but throughput and quality and amount of obtained information are limited. On the other hand, a technique of interaction analysis using liquid chromatography mass spectrometry (LC-MS) has been developed.

By reacting a protein having a higher order structure with an agent capable of chemically modifying the protein for a short time, only functional groups exposed on the surface can be selectively modified without modifying functional groups present inside the protein molecule. By using this, it has been known that information on a higher order structure can be obtained by peptide mapping using LC-MS for a modified protein (WO 2015/179714 A1). In addition, it has also been reported that the presence or absence of formation of a protein complex can be determined by applying such a technique to a protein complex (Chem. Rev. 2007, 107, 3514-3543).

SUMMARY OF THE INVENTION

However, the above-described analysis method has a problem that a long time is required for pretreatment prior to analysis. That is, a method for pretreating at high speed in protein analysis has been required.

As a result of various studies in view of the above problem, the present inventors have found that by using a protease having many types of cleavage sites in protein analysis, pretreatment can be performed in a significantly shorter time as compared with conventional methods. In addition, it is preferable to use a heat-resistant enzyme as the protease, and in that case, pretreatment can be performed at a high temperature.

According to the present invention, pretreatment for analysis of proteins can be completed in a short time. By rapidly determining the higher order structure of the protein using the method of the present invention, the presence or absence of denaturation of the protein can be confirmed, and a factor that can contribute to stability of the protein can be found. Furthermore, by the method of the present invention, substances that can interact with proteins can be identified, and substances useful as, for example, pharmaceuticals can be found.

DESCRIPTION OF THE PREFERRED EMBODIMENTS

Figure 1:
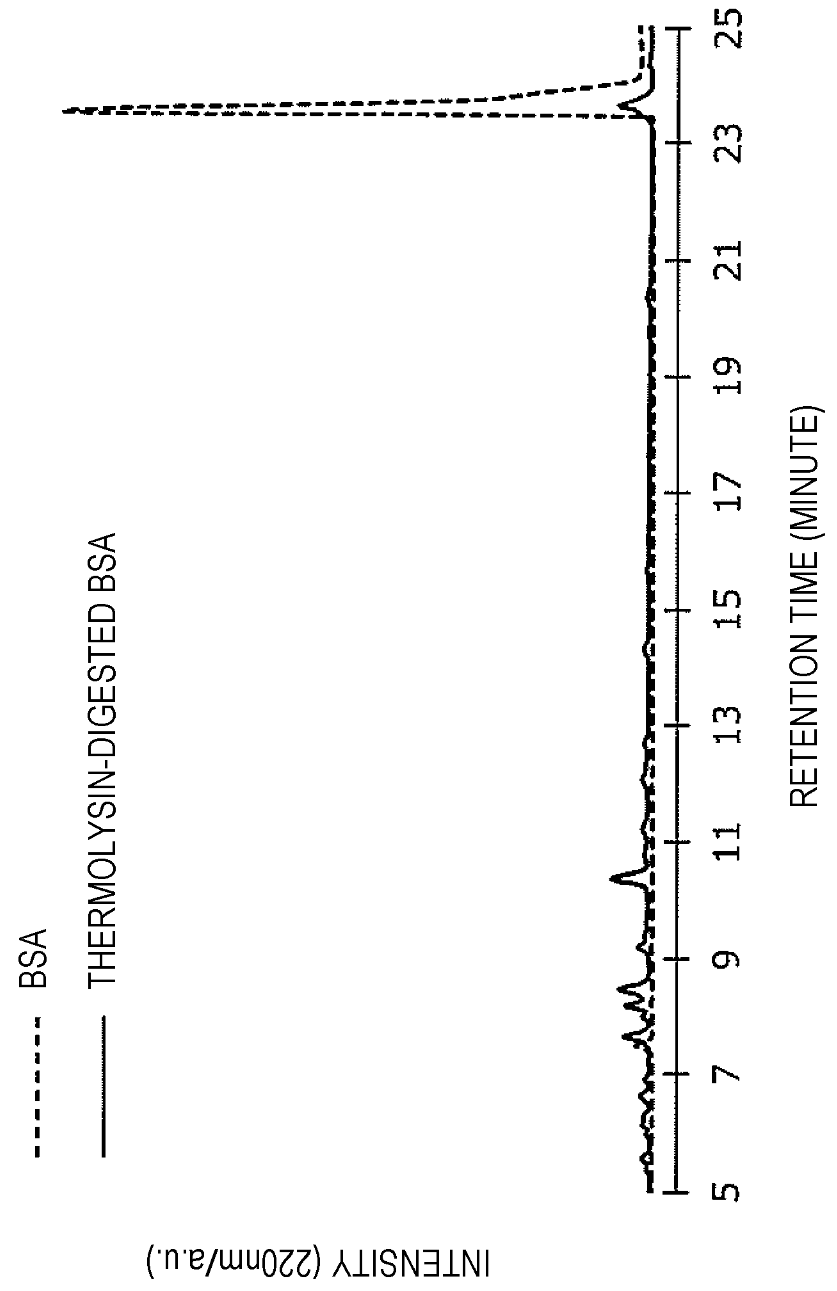
FIG. 1 shows results of HPLC analysis of peptides when a BSA aggregate was treated with thermolysin at 80° C. (solid line) according to the present invention and when the BSA aggregate was not treated (dotted line), and the vertical axis represents absorbance at 220 nm.
Figure 2:
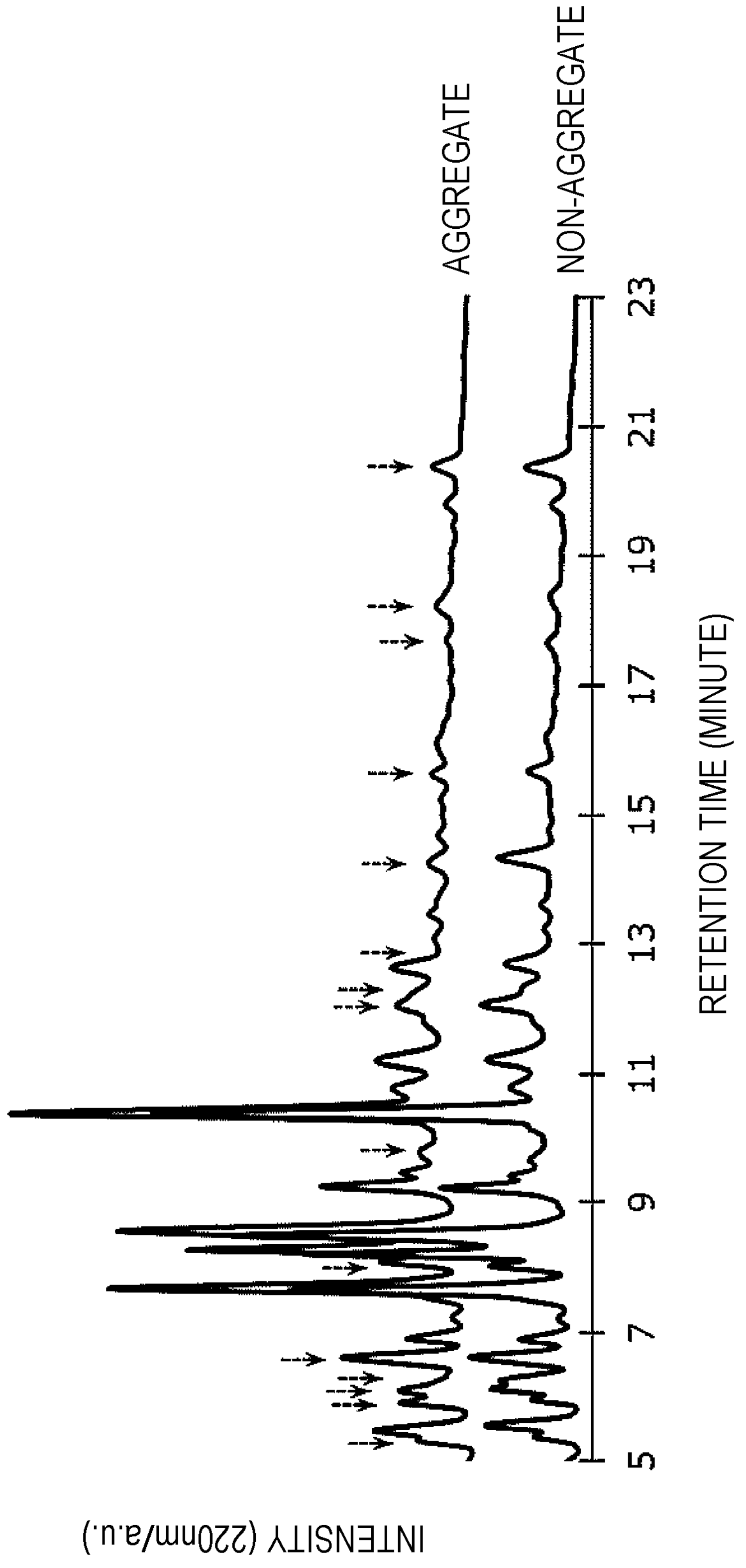
FIG. 2 shows results of HPLC analysis of peptides obtained by pretreating the BSA aggregate and a non-aggregate respectively by the method of the present invention, arrows indicate peaks with significant differences between the aggregate and the non-aggregate, and the vertical axis represents absorbance at 220 nm.

Hereinafter, embodiments of the present invention will be specifically described, but the present invention is not limited to these descriptions, and those skilled in the art can make various alterations within the scope of the technical idea disclosed in the present specification.

The present invention relates to a pretreatment method in protein analysis, and a method for analyzing a protein using the method. Specifically, the present invention provides a pretreatment method for structural analysis of a protein, the pretreatment method including chemical modifying and fragmenting a protein to be analyzed, wherein a protease having four or more cleavage sites is used in the fragmenting. The method of the present invention is intended to perform chemical modifying and fragmenting in a liquid on a sample containing a protein.

The "protein" herein may also include small and medium molecules, sometimes referred to as peptides and polypeptides. In addition, the "protein" may include, but is not limited to, for example, a glycoprotein formed by binding to a sugar, a nuclear protein formed by binding to a nucleic acid, and the like. The protein may also be a naturally occurring protein or a synthesized protein, and may further include a protein in which the following complex is formed.

An object of the method of the present invention is, but is not limited to, to analyze a higher order structure of a protein whose amino acid sequence as a primary structure is known, for example. Here, the higher order structure includes a three-dimensional structure of a protein itself and a complex structure obtained by interaction between a plurality of identical proteins or different proteins.

Specifically, the method of the present invention can be used for analysis in which amino acids present on the surface of the protein to be analyzed are identified and information on the three-dimensional structure is obtained. For example, since a protein undergoes a structural change when denatured, the presence or absence of denaturation can be confirmed.

In addition, the higher order structure of a protein may change depending on whether the protein is present alone or forms a complex. Therefore, the method of the present invention can be used for analysis for determining whether or not a protein molecule to be analyzed forms a complex (protein complex) with another substance. The protein complex is a state in which a protein (including a peptide and a polypeptide) forms an association with another substance. Examples thereof include, but are not limited to, a complex of a protein and a ligand, a complex of an enzyme protein and a substrate, a complex of a nucleic acid and a protein, a complex of a protein and a peptide, a complex of an antibody protein and an antigen, an aggregate of the same protein, and an association of subunits. The complex may be formed by a covalent bond or a non-covalent bond, for example, a hydrogen bond, a hydrophobic bond, an electrostatic interaction, or the like.

The purpose of determining the presence or absence of formation of a protein complex is not limited, but can be used for screening of candidate substances in pharmaceutical development, and the like. False positives are often problematic when screening peptides capable of recognizing specific proteins. For example, in a phage display method, even a substance that does not actually have an intended interaction may remain as a candidate. On the other hand, if information on the state of complex formation between the protein and the candidate substance can be quickly obtained, false positives can be excluded and screening can be efficiently advanced. In addition, the present invention can also be used for screening of a candidate structure of a medium-molecular pharmaceuticals.

The pretreatment method in the method for analyzing a protein provided in the present invention includes chemical modifying and fragmenting.

<Chemical Modifying>

In the chemical modifying, a reagent having high reactivity is reacted with a protein to be analyzed only for a short time, so that chemical modification reflecting an actual complex formation state in a solution is advanced.

In the chemical modifying, modification is preferentially advanced to a highly reactive site among functional groups in a protein. A highly reactive site depends on a higher order structure, thus when the higher order structure is changed due to denaturation or formation of a complex, the modification state changes accordingly. Therefore, denaturation or formation of a complex can be determined by analyzing the modification state. In particular, it is important to determine the formation of a complex at high speed, as described above.

For example, whether or not a protein to be analyzed and a candidate peptide having unknown binding to the protein form a complex can be determined as follows.

When a complex is not formed, the modification state obtained by the chemical modifying is substantially equivalent to that when each of the protein to be analyzed and the candidate peptide is independently chemically modified alone, and thus when the difference in the analysis result is within the range of measurement error as compared with the results when each is independently chemically modified, it can be determined that a complex is not formed.

On the other hand, when the protein to be analyzed and the candidate peptide form a complex, the modification state may be changed because local environment is changed at a site involved in complex formation or its periphery, as compared with the independent state. In addition, when an allosteric effect occurs due to complex formation, the modification state may change because the structure changes at a site far from the site involved in complex formation in the protein to be analyzed. Therefore, when the difference in the analysis result is clear (out of the range of measurement error) as compared with the results when each is independently chemical modified, it can be determined that a complex is formed. In this case, it can be determined that the periphery of a site having a large difference in the analysis result is involved in complex formation (a binding site with the candidate peptide or a site affected by an allosteric effect).

The analysis result can be confirmed, for example, as a value obtained by calculating a modification rate of a specific amino acid residue (a ratio at which a specific amino acid residue is modified in a specific protein in a sample). For example, the presence or absence of complex formation can be observed as a difference in the modification rate of specific amino acid residues. Regarding the difference in modification rate, the modification rates of a single amino acid residue may be compared, or the modification rates of a plurality of amino acid residues may be compared and an average value of the differences in modification rates may be calculated in some cases.

In the method of the present invention, the reaction used for chemical modification is not limited. Examples thereof include modification of a nucleophilic amino acid residue (histidine, lysine, serine, threonine, tyrosine, and the like) using an electrophile such as diethylpyrocarbonate (DEPC) or succinimide ester, oxidation of an amino acid residue using photolysis of hydrogen peroxide, carbene insertion into an amino acid residue using photolysis of diazirine, selective modification of tryptophan using [(2-hydroxy-5-nitrophenyl)methyl]dimethylsulfonium bromide (HNSB), and hydrogen deuterium exchange. It is not always necessary to use irreversible chemical modification, but from the viewpoint of the amount of information to be obtained and reproducibility, it is preferable to have stability that can be sufficiently detected in a series of analyses. In addition, it is desirable that the reaction conditions are simple.

Examples of a method in which the chemical modification has certain stability and the reaction conditions are simple include modification of a nucleophilic amino acid residue using an electrophile. Examples of the electrophile include a carbonyl compound having a preferable leaving group and an electron-deficient multiple bond compound, but are not limited thereto. Examples of the carbonyl compound having a preferable leaving group include a pyrocarbonate compound such as DEPC, an active ester compound such as succinimide ester, carbonyl imidazole, carboxylic anhydride, and carboxylic halide. Examples of the electron-deficient multiple bond compound include carbodiimide, maleimide, isocyanate, and isothiocyanate. The chemically modified residue can be detected by measuring the absorbance characteristic of the reagent used for chemical modification.

<Fragmenting>

In the fragmenting, the chemically modified protein is fragmented to put into an analyzable state. The means for fragmentation is preferably, but not limited to, hydrolysis using a protease (also described herein as "enzyme digestion").

In the conventional peptide mapping technique, a highly specific protease such as trypsin, chymotrypsin or Lys-C is used. It is generally known that proteases cleave C-terminal side or N-terminal side of each unique amino acid residue, and the term "highly specific protease" as used herein refers to a protease having a small number of types as cleavable sites. When higher reaction conditions are set by adjusting the amount ratio between the enzyme and the substrate, the reaction temperature, the reaction time, and the like, the number of cleavable sites may increase. Therefore, in the present specification, the site that is generally considered in the art to be cleaved for each enzyme is described as a "cleavage site" or a "preferential cleavage site".

For example, trypsin preferentially cleaves C-terminal sides of lysine and arginine (preferential cleavage site: 2). Chymotrypsin preferentially cleaves C-terminal sides of phenylalanine, tyrosine, and tryptophan (preferential cleavage site: 3). Lys-C preferentially cleaves C-terminal side of lysine (preferential cleavage site: 1). When a protein is degraded using these enzymes, the resulting peptide will have a longer amino acid length, which may be suitable for identifying the protein from which the peptide is derived. Therefore, it is advantageous to use these enzymes, for example, when identifying a protein whose primary structure is unknown.

On the other hand, since these enzymes have few preferential cleavage sites, it is necessary to denature or reduce the protein for digestion to increase the contact probability between the enzyme and the cleavage site. For example, in the case of denaturing the protein for digestion, applying a denaturant such as urea, arginine, or a surfactant is required, and removing the denaturant is further required, which causes to require a long time for the pretreatment. In addition, in the case of reduction, allowing a reducing agent such as DTT or TCEP to act, alkylation of capping the reduced site, inactivating or removing an excess reagent, and the like are required, which causes to require a long time for the pretreatment.

The method of the present invention is intended to analyze the higher order structure of proteins as described above. In this case, it is not necessary to use a highly specific protease as described above. Conversely, as a result of studies by the present inventors, it has been found that by using an enzyme having lower specificity, that is, having a relatively large number of preferential cleavage sites, denaturation using a denaturant and reduction can be omitted, and pretreatment can be performed in a short time.

Examples of the protease that can be suitably used in the method of the present invention include thermolysin (preferentially cleaves N-terminus of hydrophobic amino acid residues such as leucine, phenylalanine, valine, isoleucine, alanine, and methionine, preferential cleavage site: 6), elastase (preferentially cleaves C-terminal side of alanine, valine, serine, glycine, leucine, and isoleucine, preferential cleavage site: 6), and pepsin (preferentially cleaves C-terminal side of phenylalanine, leucine, tyrosine, and tryptophan, preferential cleavage site: 4).

When these enzymes are used, proteins can be digested without requiring denaturation or reduction which needs a long time. The enzyme that can be suitably used in the method of the present invention is not particularly limited, but an enzyme having 4 or more preferential cleavage sites is considered to be preferable. Even when the number of preferential cleavage sites is 3 or less, the number of preferential cleavage sites may increase in a natural enzyme due to genetic recombination, chemical modification, or the like, and thus such an enzyme can also be used as an enzyme having a relatively large number of preferential cleavage sites.

The upper limit of the number of preferential cleavage sites is not limited. If there are too many preferential cleavage sites, the resulting fragment may be too short and difficult to be analyzed, but enzymes having any number of preferential cleavage sites can be used as long as they can be analyzed. It is also conceivable that the coverage of the amino acid sequence is reduced by shortening the obtained fragment, but in order to determine the presence or absence of formation of a protein complex, only a change in the chemical modification state needs to be detected, and therefore a high coverage is not necessarily required. However, from the viewpoint of ease of analysis and reproducibility, it is considered practical that the number of preferential cleavage sites is about 10 or less. There is a case where reactivity with a protease is affected by chemical modification of an amino acid residue, but the number of preferential cleavage sites in such a case may be for a protein not chemically modified. Examples of the case where reactivity is affected by chemical modification include a case where lysine is chemically modified so that it is difficult to be cleaved by trypsin.

The reaction temperature in the fragmenting can be increased within a range in which enzyme digestion is not adversely affected. This is because digestion is completed in a shorter time at a higher temperature as long as the enzyme activity is sufficient.

A general enzyme reaction is often performed at about 30 to 50° C. because the enzyme activity decreases at a high temperature, and for example, trypsin is generally used at about 37° C. in an existing peptide mapping technique. However, when the enzyme digestion is performed under such conditions, it generally takes about 2 to 18 hours, depending on the amount of trypsin to be used. On the other hand, the fragmenting can be completed in a short time by performing enzyme digestion at a high temperature using a heat-resistant enzyme. As the heat-resistant enzyme, an enzyme having heat resistance in a natural state may be used, or an enzyme that has acquired heat resistance by genetic recombination, chemical modification, or the like may be used.

Examples of the heat-resistant protease include thermolysin, genetically modified thermolysin, chemically modified thermolysin, genetically modified elastase, chemically modified elastase, genetically modified pepsin, and chemically modified pepsin. The enzyme digestion temperature when such a heat-resistant enzyme is used is preferably 60 to 99° C., more preferably 65 to 95° C., and further preferably 70 to 90° C. In the case of enzymatic digestion at a high temperature using a heat-resistant enzyme, an effect of improving the reactivity can also be expected by thermal denaturation of a protein to be fragmented.

The enzyme used in the fragmenting may be used in a solution state or may be immobilized on a carrier. When the enzyme is immobilized on the carrier, autolysis of the enzyme can be prevented, so that there is no decrease in activity due to autolysis even when the enzyme is used at a high concentration. For example, an immobilized thermolysin on which the above-described thermolysin or the like is immobilized can be used. The immobilized enzyme also has an advantage of being easily separated from the sample. Examples of the carrier include, but are not limited to, magnetic beads (Absolute Mag (trademark) Amine Magnetic Nanoparticles, CD Bioparticles), silica beads (silica gel, Sigma), metal beads (steel ball SUS304 mm size), resin beads (Melamine resin beads Supelco), and polysaccharide beads (Alginate and cellulose beads).

Solvent, pressure, and the like in the fragmenting are not limited. An organic solvent, a salt, a surfactant, and the like can be used within ranges in which sufficient enzyme activity can be obtained. In addition, pressurization/depressurization may be performed within ranges in which sufficient enzyme activity can be obtained. Since there is also an example in which the enzyme activity is improved by pressurization, pressurization can be an option for shortening the digestion time, but atmospheric pressure or the like may be used.

<Analyzing>

The method for analyzing a protein provided in the present invention includes an analyzing in addition to the above-described steps. In the analyzing, the modification state of chemically modified and fragmented protein can be quantitatively evaluated. Since a sample containing a chemically modified and fragmented protein is a complex mixture, it is suitable to separate and analyze the protein.

For example, the chemically modified and fragmented protein in the sample can be separated using liquid chromatography (LC). LC separation mode is not limited. Separation modes such as reverse phase, normal phase, pi electron density, hydrophobic and ionic mixed mode, size exclusion, anion exchange, cation exchange, and affinity can be selected as necessary, or separation may be performed using a plurality of columns. The solvent conditions and pressure in LC are also not limited. HPLC or UPLC may be used, or capillary column LC may be used. As another example, separation can also be performed using electrophoresis.

The method for quantitatively evaluating the modification state of the protein is not limited. For example, by using mass spectrometry as a quantitative evaluation method, it is easy to identify a chemical species obtained by fragmentation and to quantify the modification rate. Mass spectrometry can be combined, for example, with separation by LC (LC-MS). In addition, when an affinity label is imparted by chemical modification, separation and analysis can be performed simultaneously by detecting a component obtained by affinity separation. On the other hand, it is also possible to quantitatively evaluate only the relative change in the modification state without identifying the components in the chemically modified and fragmented sample. For example, by using a site exhibiting characteristic light absorption properties or a site exhibiting fluorescence properties in chemical modification, it is possible to sufficiently quantitatively evaluate the relative change in the modification state only by LC with absorption detection or fluorescence detection. In addition, as long as the components in the chemically modified and fragmented sample are sufficiently separated, it is possible to detect a quantitative change in the modification state from the change in the shape of an LC chart without characteristic light absorption, fluorescence, or the like. When the modification rate can be evaluated with sufficient quantitativity even in a state in which the components are not separated, the components may not be separated. As a method for evaluating the modification state in a non-separated state, NMR or the like is considered. The structure of a protein of interest can be identified by detecting chemically modified residues and fragmented proteins using the method of the present invention.

The method provided in the present invention can further include the following steps in addition to the steps described above.

<Quenching>

As an example, quenching can be included after the chemical modifying. It is possible to prevent the reaction with the digestive enzyme used in the fragmenting by inactivating the reagent that has not reacted although used for the chemical modification. Means of inactivation can be appropriately selected by those skilled in the art depending on the chemical modification used, and is not limited.

For example, when an electrophilic reactant is used for chemical modification, a nucleophile having a nucleophilic heterocyclic structure such as imidazole can be added as a quencher.

When photolysis of hydrogen peroxide is used for chemical modification, a sacrificial agent such as a hydrogen peroxide decomposing enzyme or methionine that reacts with a secondary oxide can be added as a quencher.

The quencher is not limited, but from the viewpoint of speeding up the pretreatment, it is preferable that the quencher is that easily removed in the subsequent step or that hardly affects the subsequent step. As an example of the condition that is easily removed in the subsequent step, the quencher is heterogeneous or is likely to be heterogeneous.

Examples of the heterogeneous quencher include a quencher supported on a carrier and a poorly soluble quencher. Examples thereof include a particle having an imidazole moiety on the surface, and a particle having catalase immobilized on the surface. Examples of the quencher which is likely to be heterogeneous include a quencher which is likely to be adsorbed to an adsorbent or the like and a quencher which is likely to decrease the solubility. Examples of the quencher which is likely to be adsorbed to an adsorbent or the like include polymers such as polyhistidine and polyvinylimidazole having an imidazole partial structure. It is known that a molecule having a plurality of imidazole partial structures is easily adsorbed to, for example, an adsorbent on which Ni ions are chelated and supported. Examples of the quencher which is likely to decrease the solubility include a quencher which has a temperature-responsive site and changes the solubility, a quencher which has a chelate site and is likely to be precipitated by a precipitating agent, and a quencher which is hydrophobized and has reduced solubility in a pH-dependent manner.

<Purifying>

As another example, purifying can be included between the chemical modifying and the fragmenting. When a by-product of the reaction reagent used in the chemical modifying or a chemical species generated by inactivation of the reaction reagent remains, there is a risk of interfering with the activity of the digestive enzyme used in the fragmenting. Therefore, removing them by purification can be added. The purification method is not limited, but from the viewpoint of speeding up the pretreatment, it is possible to utilize being heterogeneous as described above. For example, the solution of the sample obtained by chemical modification and the quencher can be separated by filtration or centrifugation. When a magnetic substance is used as a carrier of the quencher or a carrier of an adsorbent, magnetic separation can also be performed. In the above-described example, examples include a magnetic particle having an imidazole moiety on the surface, a magnetic particle having catalase immobilized on the surface, and the like.

<Buffer Exchanging>

As yet another example, buffer exchanging can be included after the fragmenting. Since the solvent conditions used for chemical modification and fragmentation are not necessarily suitable for analysis, buffer exchange can be appropriately performed by a technique such as dialysis, a desalting column, or solid phase extraction.

<Enzyme Removing>

As another example, enzyme removing can be included after the fragmenting. In particular, when an immobilized enzyme is used, the enzyme can be easily removed by filtration, centrifugation, magnetic separation, or the like, depending on the properties of the carrier.

<Storing>

As yet another example, storing can be included after the fragmenting. By, for example, cooling, freezing, freeze-drying, or the like of the fragmented protein, it is possible to prevent the state from changing before analysis.

<Determining>

When the method for analyzing a protein provided in the present invention is used for determining the presence or absence of formation of a protein complex, determining is included.

For example, in the determining, analysis results of a sample containing a protein and a candidate substance in a mixed state and a sample containing a protein alone can be compared. Alternatively, the analysis result in the sample containing a protein and a candidate substance can be compared with the analysis result in the sample containing a protein and a reference substance (substance for which whether a complex with the protein is formed or not is known).

The comparison may be to determine whether or not there is a significant difference between the respective analysis results. The method for determining the significant difference is not limited, and for example, determination may be made by focusing on the modification rate of a specific functional group, or determination may be made by focusing on the modification rate of a plurality of functional groups. Also, the determination may be made based on the standard deviation obtained by a plurality of trials, or the significant difference may be determined using statistical tests. Statistical tests include, but are not limited to, t-test. In the statistical tests, the significance level can be arbitrarily determined as long as a reliable result is obtained.

EXAMPLES

Comparative Example 1

Using BSA aggregates prepared by heat-treating globulin-free BSA (Wako) as a biomolecular complex at 80° C. for 30 minutes, DEPC as an electrophile, and trypsin (TPCK-treated trypsin, Sigma-Aldrich) as a digestive enzyme, a conventional pretreatment method was examined. BSA is a protein composed of 583 amino acids listed as 3V03 in a database such as protein data bank (PDB), and those skilled in the art can obtain information such as its amino acid sequence (see also, for example, www.rcsb.org/structure/3v03).

To the BSA aggregates (10 mg/mL, 500 μL) was added a solution of DEPC in acetonitrile (11 mg/mL, 10 μL), and the mixture was heated at 37° C. for 5 minutes. Thereafter, an aqueous imidazole solution (95 mg/mL, 25 μL) was added, and the mixture was heated at 37° C. for 30 minutes. The resulting solution of DEPC-modified BSA was denatured with urea, the urea was removed by ultrafiltration, then reductive alkylation was performed with a DTT/IAA system, and the reagent residue was removed again by ultrafiltration.

After adjusting the concentration of the resulting solution with Tris buffer, the trypsin solution was added at a ratio of 25:1 to BSA (BSA: enzyme, the same applies hereinafter), the mixture was heated at 37° C. for 12 hours, and then the resulting solution was buffer-exchanged and subjected to LC-MS analysis under the following conditions.

LC: ODS column, 40° C., water/acetonitrile+0.1% formic acid

MS: TOF, ESI positive

When BSA aggregates without enzyme treatment are analyzed under the above conditions, a single peak is observed at around a retention time of 24 minutes. With this peak intensity as an initial state, the reduction rate of the peak intensity was calculated as digestibility. As a result, the digestibility of BSA was 90% or more, and the time required for the pretreatment was 18 hours in total.

Example 1

A pretreatment method without reductive alkylation was studied using BSA aggregates as biomolecular complexes, DEPC as an electrophile, and thermolysin (Promega) as a digestive enzyme. To the BSA aggregates (10 mg/mL, 500 μL) was added a solution of DEPC in acetonitrile (11 mg/mL, 10 μL), and the mixture was heated at 37° C. for 5 minutes. Thereafter, an aqueous imidazole solution (95 mg/mL, 25 μL) was added, and the mixture was heated at 37° C. for 30 minutes.

After adjusting the concentration of the resulting solution with Tris-$CaCl_2$ buffer, the thermolysin solution was added at a ratio of 25:1 to BSA, the mixture was heated at 80° C. for 30 minutes, and then the resulting solution was buffer-exchanged, and analyzed in the same manner as in Comparative Example 1. As a result, the digestibility of BSA was 80% or more as calculated from HPLC, and the time required for the pretreatment was 1.5 hours in total, which was shorter than that in the conventional method.

The resulting solution was subjected to HPLC analysis (absorbance at 220 nm) in the same manner as in Comparative Example 1 using a C18 column (Cosmosil Protein-R) under gradient elution conditions of water/acetonitrile=10:90 to 90:10.

As shown in FIG. 1, when the fragmenting was performed at a high temperature using thermolysin, the peak observed at a retention time of about 24 minutes almost disappeared, and the peak of the fragmented peptide was observed at a shorter retention time.

Comparative Example 2

Pretreatment at a general temperature was examined using thermolysin. Conditions were similar to those in Example 1 except that the reaction was performed at 37° C. To the BSA aggregates (10 mg/mL, 500 μL) was added a solution of DEPC in acetonitrile (11 mg/mL, 10 μL), and the mixture was heated at 37° C. for 5 minutes. Thereafter, an aqueous imidazole solution (95 mg/mL, 25 μL) was added, and the mixture was heated at 37° C. for 30 minutes.

After adjusting the concentration of the resulting solution with Tris-$CaCl_2$ buffer, the thermolysin solution was added at a ratio of 25:1 to BSA, the mixture was heated at 37° C. for 30 minutes, and then the resulting solution was buffer-exchanged and subjected to LC-MS analysis. As a result, the digestibility of BSA was 10%, and fragmentation at 37° C. using thermolysin was not sufficient pretreatment.

Comparative Example 3

Pretreatment at a high temperature was examined using a non-heat-resistant digestive enzyme. Conditions were similar to those in Example 1 except that trypsin was used. To the BSA aggregates (10 mg/mL, 500 μL) was added a solution of DEPC in acetonitrile (11 mg/mL, 10 μL), and the mixture was heated at 37° C. for 5 minutes. Thereafter, an aqueous imidazole solution (95 mg/mL, 25 μL) was added, and the mixture was heated at 37° C. for 30 minutes.

After adjusting the concentration of the resulting solution with Tris buffer, the trypsin solution was added at a ratio of 25:1 to BSA, the mixture was heated at 80° C. for 30 minutes, and then the obtained solution was buffer-exchanged and subjected to LC-MS analysis. As a result, the digestibility of BSA was less than 5%, and the pretreatment was not sufficient.

Comparative Example 4

Pretreatment without reductive alkylation using an enzyme having a small number of preferential cleavage sites was examined. To the BSA aggregates (10 mg/mL, 500 μL) was added a solution of DEPC in acetonitrile (11 mg/mL, 10 μL), and the mixture was heated at 37° C. for 5 minutes. Thereafter, an aqueous imidazole solution (95 mg/mL, 25 μL) was added, and the mixture was heated at 37° C. for 30 minutes.

After adjusting the concentration of the resulting solution with Tris buffer, the trypsin solution was added at a ratio of 25:1 to BSA, the mixture was heated at 37° C. for 1 hour, and then the obtained solution was buffer-exchanged and subjected to LC-MS analysis. As a result, the digestibility of BSA was less than 10%, and the pretreatment was not sufficient.

Example 2

In addition to the conditions of Example 1, a pretreatment method in which simple removing of the quencher in the chemical modifying was added was examined. As a quencher, polyvinyl imidazole was used.

To the BSA aggregates (10 mg/mL, 500 μL) was added a solution of DEPC in acetonitrile (11 mg/mL, 10 μL), and the mixture was heated at 37° C. for 5 minutes. Thereafter, an ethanol solution of polyvinyl imidazole (10 mg/mL, 25 μL) was added thereto as a first adsorbent, and the resulting mixture was heated at 37° C. for 30 minutes. Ni-supported polysaccharide beads, HisTrap™, as a second adsorbent were added to the resulting solution, and the mixture was stirred for 10 minutes. After removing the supernatant and adjusting the concentration with Tris-$CaCl_2$) buffer, the thermolysin solution was added at a ratio of 25:1 to BSA, the mixture was heated at 80° C. for 30 minutes, and then the resulting solution was buffer-exchanged and subjected to LC-MS analysis. As a result, the digestibility of BSA was 90% or more, and the time required for the pretreatment was 1.7 hours in total, which was shorter than that in the conventional method.

Example 3

In addition to the conditions of Example 1, a pretreatment method in which simple removing of the quencher in the chemical modifying was added was examined. As a quencher, magnetic beads having an amino group on the surface, Sicaster®-M, were used.

To the BSA aggregates (10 mg/mL, 500 L) was added a solution of DEPC in acetonitrile (11 mg/mL, 10 μL), and the mixture was heated at 37° C. for 5 minutes. Thereafter, a Tris dispersion of Sicaster®-M (500 μL) was added as an adsorbent, and the mixture was stirred for 30 minutes. After the magnetic beads were precipitated using a magnet, the supernatant was collected and the concentration was adjusted with Tris-$CaCl_2$ buffer. Thereafter, the thermolysin solution was added at a ratio of 25:1 to BSA, the mixture was heated at 80° C. for 30 minutes, and then the resulting solution was buffer-exchanged and subjected to LC-MS analysis. As a result, the digestibility of BSA was 90% or more, and the time required for the pretreatment was 1.7 hours in total, which was shorter than that in the conventional method.

Example 4

Pretreatment and analysis similar to those in Example 1 were performed on BSA that was not an aggregate (globulin-free BSA, Wako), and the results were compared to determine formation of aggregates as complexes.

The analysis of Example 1 and the present example was performed with N=3, respectively, and a t-test was performed on representative peaks in HPLC. As a result, 6 or more peaks having a significant difference probability of 99% or more were found (for example, ADEKK (SEQ ID NO: 1), LPK, IQK, AKD, FDK, and LKT), and it was determined that there was a significant difference in modification rate.

Next, when a residue from which a peak having a significant difference was derived was identified by LC-MS, Lys131, Lys180, Lys204, Lys322, Lys375, Lys544, and the like were identified as residues having a significant difference in modification rate.

```
                    SEQUENCE LISTING


Sequence total quantity: 1
SEQ ID NO: 1           moltype = AA  length = 5
FEATURE                Location/Qualifiers
source                 1..5
                       mol_type = protein
                       organism = Bos taurus
SEQUENCE: 1
ADEKK                                                     5
```

What is claimed is:

1. A pretreatment method for structural analysis of a protein, the method comprising:

a) chemically modifying a protein to be analyzed; and b) fragmenting the protein to be analyzed, wherein in step a), chemically modifying is a chemical modification of the protein by an electrophile, wherein in step b), the protein is treated at a temperature of 60° C. to 99° C. in the presence of a heat-resistant protease that has four or more cleavage sites and is soluble or immobilized on a carrier, and wherein the method further comprises removing one or more selected from the electrophile, a by-product of the electrophile, a quencher for the electrophile, and a by-product of the quencher for the electrophile, using an adsorbent.

2. The method according to claim 1, wherein the heat-resistant protease contains one or more selected from thermolysin, recombinant thermolysin, modified thermolysin, elastase, recombinant elastase, modified elastase, pepsin, recombinant pepsin, and modified pepsin.

3. The method according to claim 1, wherein the electrophile is a carbonyl compound comprising a leaving group or an electron-deficient multiple bond compound.

4. The method according to claim 1, wherein the adsorbent is a polymeric or insoluble adsorbent.

5. The method according to claim 1, further comprising analyzing the fragmented protein of step b), wherein the analyzing is performed by one or more analysis methods selected from liquid chromatography, mass spectrometry, liquid chromatography mass spectrometry, and NMR.

* * * * *